United States Patent
Hussain et al.

(10) Patent No.: US 6,200,591 B1
(45) Date of Patent: Mar. 13, 2001

(54) METHOD OF ADMINISTRATION OF SILDENAFIL TO PRODUCE INSTANTANEOUS RESPONSE FOR THE TREATMENT OF ERECTILE DYSFUNCTION

(76) Inventors: Anwar A. Hussain, 886 McMeekin Pl., Lexington, KY (US) 40502; Lewis W. Dittert, 4999 Hartland Pkwy., Lexington, KY (US) 40515

(*) Notice: Subject to any disclaimer, the term of this patent is extended or adjusted under 35 U.S.C. 154(b) by 0 days.

(21) Appl. No.: 09/208,439

(22) Filed: Dec. 10, 1998

Related U.S. Application Data

(60) Provisional application No. 60/090,740, filed on Jun. 25, 1998.

(51) Int. Cl.$^7$ .................................................. A61F 13/02
(52) U.S. Cl. ................................................................ 424/434
(58) Field of Search .................................... 424/434, 451, 424/464

(56) References Cited

FOREIGN PATENT DOCUMENTS

| | | |
|---|---|---|
| 0 463 756 | 1/1992 | (EP). |
| 0 951 908 | 10/1999 | (EP). |
| 0 967 214A1 | 12/1999 | (EP). |
| 98 19672 | 5/1998 | (WO). |
| 98 30209 | 7/1998 | (WO). |
| 99 02161 | 1/1999 | (WO). |
| 99 30688 | 6/1999 | (WO). |
| 99 27905 | 10/1999 | (WO). |

OTHER PUBLICATIONS

Gemalmaz et al, "Sildenafil (Viagra) enahnces apomorphine-induced intra-cavernosus pressures in awake rats", Journal of Urology, vol. 159, No. 5, Suppl., pp. 91, May 1998.*

Notsu, Tatsuto et al: "Preparation of Therapeutic Agent for Erection Failure" *Chemical Abstracts*, vol. 130, No. 4, Jan. 25, 1999, Abstract No. XP002124208.

* cited by examiner

*Primary Examiner*—Carlos A. Azpuru
(74) *Attorney, Agent, or Firm*—Burns, Doane, Swecker & Mathis, L.L.P.

(57) ABSTRACT

This invention provides a method of rapidly and reliably delivering sildenafil, or derivatives thereof, alone or in combination with other compounds, to the systemic circulation by administration via the nasal route so as to produce virtually instantaneous onset of beneficial effects in the treatment of erectile dysfunction. The present invention further provides pharmaceutical compositions comprising sildenafil, or derivatives thereof, and/or pharmaceutically acceptable salts thereof in a variety of unique pharmaceutical dosage forms, with and without apomorphine.

12 Claims, 1 Drawing Sheet

METHOD OF ADMINISTRATION OF SILDENAFIL TO PRODUCE INSTANTANEOUS RESPONSE FOR THE TREATMENT OF ERECTILE DYSFUNCTION

This application is a Continuation-in-Part of Provisional Application Ser. No. 60/090,740, filed Jun. 25, 1998.

BACKGROUND OF THE INVENTION

1. Field of the Invention

This invention relates to a method for greatly accelerating the rate of delivery of sildenafil, and derivatives thereof, to the central nervous system by administration via the nasal route to provide extremely rapid response in the treatment of erectile dysfunction in a patient in need of such prevention or treatment. This method provides response in less than five minutes, compared with 60 minutes or more required by the currently used oral route of administration.

2. Description of the Related Art

Male sexual dysfunction, or impotence, may be manifested in various ways: loss of desire, inability to obtain or maintain an erection, premature ejaculation, absence of emission, inability to achieve orgasm. The organic causes of erectile impotence can be grouped into endocrine, drug, local, neurologic, and vascular causes. Vascular insufficiency causes impotence because blood flow into the vascular network of the penis is insufficient to obtain (or maintain) the erect state. Likewise, occlusion in smaller vessels supplying the penis can also lead to impotence. Together with neuropathy, vascular insufficiency contributes to the impotence in many men with diabetes mellitus.

Erectile impotence or dysfunction may be defined as an inability to achieve or sustain an erection adequate for intercourse. Its prevalence is claimed to be between 2 and 7% of the human male population as a whole, and the incidence increases with age up to 50 years. Between 18 and 75% of the male population between 55 and 80 years of age are impotent. In the USA alone, for example, it has been estimated that there are up to 10 million impotent males, with the majority suffering from problems of organic rather than psychogenic origin.

Medical therapy with androgens offers little more than placebo benefit except in hypogonadal men. Surgical therapy may be useful in the treatment of decreased potency related to aortic obstruction; however, potency can be lost rather than improved after aortic operation if the autonomic nerve supply to the penis is damaged. A useful surgical technique for improvement of potency in refractory patients such as individuals with diabetic neuropathy is the implantation of a penile prosthesis, e.g., the insertion within the corpora of a small, blunt, Silastic® rod. The patient must be made aware that full erection is not produced and that the device only prevents buckling during intercourse. Furthermore, the complication rate is high in some patients. Alternatively, an inflatable prosthetic device has been devised for implantation on either side of the corpora. A connecting reservoir of material is placed in the perivesicular space and pumps are located in the scrotum. By means of these pumps the penis can be made to become nearly fully erect at the appropriate time and to relax after intercourse.

Prostaglandin E-1 (PGE-1; Alprostadil) has been employed successfully in the treatment of erectile dysfunction. Injections of 10 to 60 µg of PGE-1 directly into the corpora cavernosa of the penis have been found to be effective in producing erections sufficient to allow intercourse. The erections are reported to last 30 minutes to one hour, but the dangers associated with self-injection, e.g., infection, trauma, etc. make this treatment method highly undesirable.

PGE-1 has also been administered by placing a pellet containing 125 to 1000 µg of the drug into the male urethra using a specially-designed device. This approach, while avoiding the dangers of self-injection, still involves the danger of producing a urethral infection. Other drawbacks include difficulty in adjusting the dose, trauma to the urethra, and vaginal burning in the female partner.

Medical treatment of erectile dysfunction has been attempted using intracavernosal (i.c.) injection of vasoactive substances, and good results have been claimed with phenoxybenzamine, phentolamine, papaverine, and prostaglandin $E_1$, either alone or in combination; however, pain, priapism, and fibrosis of the penis are associated with the i.c. administration of some of these agents. Potassium channel openers (KCO) and vasoactive intestinal polypeptide (VIP) have also been shown to be active i.c., but cost and stability issues could limit development of the latter. An alternative to the i.c. route is the use of glyceryl trinitrate (GTN) patches applied to the penis, which has been shown to be effective but produces side-effects in both patient and partner.

Sublingual administration of apomorphine has been reported to restore normal erectile function through its effect on brain chemistry. However, the response requires 20 to 40 minutes following administration, and apomorphine was found to be effective in returning sexual potency only to about 70% of men whose dysfunction had psychological origins.

It has recently been discovered that inhibitors of cyclic guanosine 3',5'-monophosphate phosphodiesterases (cGMP PDEs) such as sildenafil are useful in the treatment of erectile dysfunction. As disclosed in PCT Publication WO 94/28902, the disclosure of which is hereby incorporated by reference, these compounds may be administered orally, thereby obviating the disadvantages associated with i.c. administration. However, the time to onset of action of periorally administered drugs is long and highly variable, due to differences in absorption based on a wide variety of factors, from the size and age of the patient to the interval since, and size and composition of, the last meal consumed by the patient. Currently, sildenafil must be administered orally about one hour prior to intercourse. This is a major drawback in situations where a rapid, reliable onset of effect is highly desirable for treatment to be considered optimal. Also, the long delay may lead to overdoses if the patient becomes impatient and decides to consume additional tablets in order to produce the desired effect.

Therefore, in view of the aforementioned deficiencies attendant with prior art methods of treatment of erectile impotence, it should be apparent that there still exists a need in the art for a rapid, reliable, safe and convenient method of inducing an erection in a patient in need of such treatment.

SUMMARY OF THE INVENTION

Accordingly, a major object of the present invention is to provide a method for safely and conveniently administering sildenafil to a patient in need of treatment for erectile dysfunction in order to produce a reliable response in less than five minutes. The method comprises the intranasal administration of an effective amount of sildenafil to rapidly produce an erection sufficient to allow intercourse.

The objective of the present inventors is to improve the rate of delivery of sildenafil to the systemic circulation by administering sildenafil via the nasal route in order to speed the onset of effect and reduce the dose required for its beneficial effect. According to the method of the present invention, sildenafil, or derivatives thereof, may successfully be administered five to ten minutes prior to intercourse.

Practice of the method of the present invention will also result in lower plasma concentrations of metabolites of sildenafil, and derivatives thereof, and therefore fewer side effects. Intranasal delivery will improve drug bioavailability by direct absorption into the systemic circulation, thereby avoiding extensive hepatic and/or gut wall first-pass metabolism which may significantly lower the plasma concentrations of sildenafil when it is administered orally. As a result, small doses of sildenafil, or derivatives thereof, can be administered which will result in fewer side effects, and the drug will be more tolerable and more effective in patients suffering from erectile impotence. Most importantly, since sildenafil is effective immediately following intranasal administration, the patient is able to titrate himself until he achieves the desired response, rather than overdosing himself by swallowing an excessive number of tablets.

Intranasal dosage forms containing sildenafil in combination with other drugs used in the treatment of erectile dysfunction may also be employed in the practice of this method. Such additional drugs include, but are not limited to, apomorphine, papaverine, phentolamine, and phenoxybenzamine.

With the foregoing and other objects, advantages and features of the invention that will become hereinafter apparent, the nature of the invention is further explained in the following detailed description of the preferred embodiments of the invention and in the appended claims.

DETAILED DESCRIPTION OF THE PREFERRED EMBODIMENTS OF THE INVENTION

Figure 1:
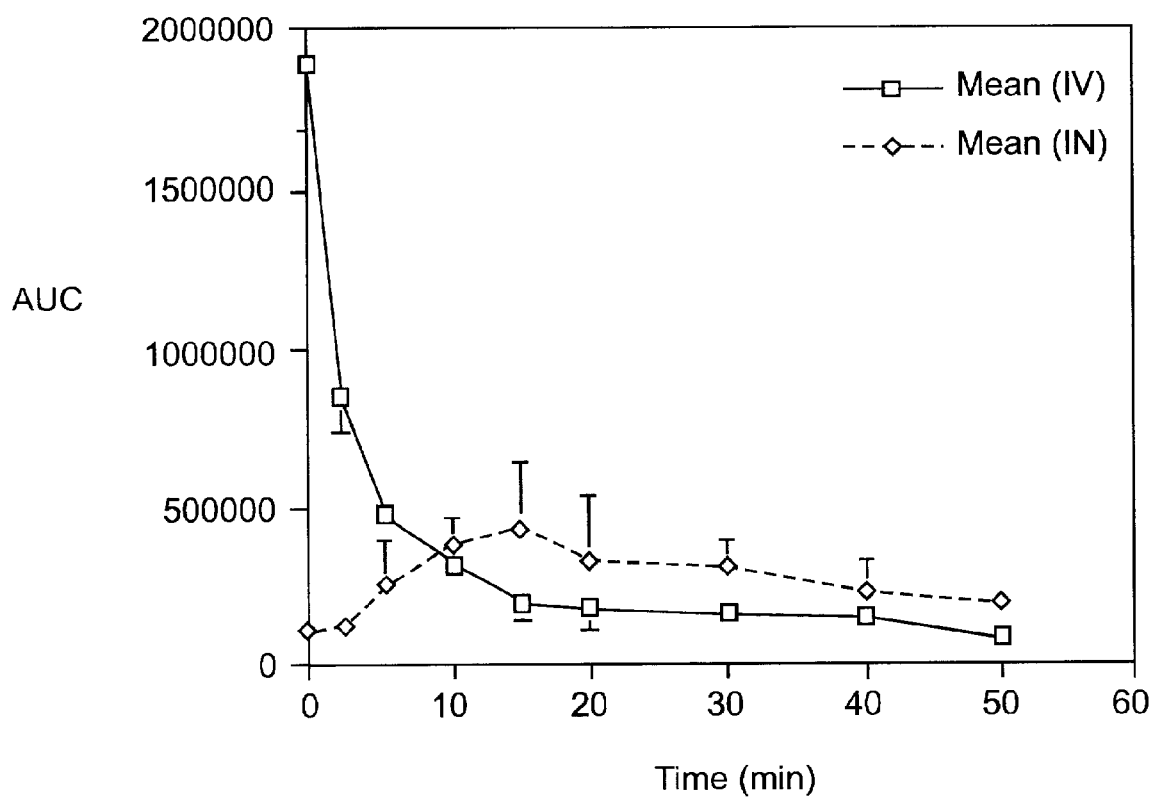
FIG. 1 represents a comparison of blood levels of sildenafil following intravenous administration to those following intranasal administration.

Thus, the present inventors have discovered a novel method for the delivery of sildenafil, or derivatives thereof, to a patient in need of such treatment, comprising the intranasal administration of sildenafil, or derivatives thereof. This method offers significant clinical advantages over the prior art. More specifically, the inventors sought to provide a rapid, reliable, safe, effective and convenient treatment for administering sildenafil, or derivatives thereof, to a patient in need of such treatment, which comprises the administration of sildenafil, or derivatives thereof, intranasally, thus providing nearly instantaneous response while avoiding the side-effects associated with oral dosage forms. Specifically, smaller doses of sildenafil, or derivatives thereof, can be administered through the nasal route, thus resulting in fewer side effects. By using the method of the present invention, which produces an instantaneous response, the drug will become more tolerable and more effective in treating patients suffering from erectile impotence.

More particularly, the present invention concerns the intranasal administration of sildenafil, or derivatives thereof, having the chemical structure of formula (I):

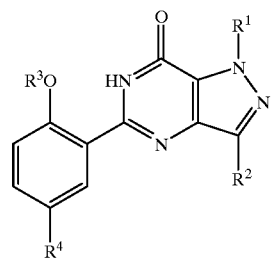

wherein
R$^1$ is H; C$_1$–C$_3$ alkyl; C$_1$–C$_3$ perfluoroalkyl; or C$_3$–C$_5$ cycloalkyl;
R$^2$ is H; C$_1$–C$_6$ alkyl optionally substituted with C$_3$–C$_6$cycloalkyl; C$_1$–C$_3$ perfluoroalkyl; or C$_3$–C$_5$ cycloalkyl;
R$^3$ is C$_1$–C$_6$ alkyl optionally substituted with C$_3$–C$_6$ cycloalkyl; C$_1$–C$_3$ perfluoroalkyl; or C$_3$–C$_5$ cycloalkyl;
R$^4$ is C$_1$–C$_4$ alkyl optionally substituted with OH, NR$^5$R$^6$, CN, CONR$^5$R$^6$, or CO$_2$R$^7$; C$_2$–C$_4$ alkenyl optionally substituted with CN, CONR$^5$R$^6$, or CO$_2$R$^7$; C$_2$–C$_4$ alkanoyl optionally substituted with NR$^5$R$^6$; (hydroxy)C$_2$–C$_4$ alkyl optionally substituted with NR$^5$R$^6$; (C$_2$–C$_3$ alkoxy)C$_1$–C$_2$ alkyl optionally substituted with OH or NR$^5$R$^6$; CONR$^5$R$^6$, CO$_2$R$^7$; halo; NR$^5$R$^6$; NHSO$_2$NR$^5$R$^6$; NHSO$_2$R$^8$; SO$_2$NR$^9$R$^{10}$; or phenyl, pyridyl, pyrimidinyl, imidazolyl, oxazolyl, thiazolyl, thienyl or triazolyl any of which is optionally substituted with methyl;
R$^5$ or R$^6$ are each independently H or C$_1$–C$_4$ alkyl, or together with the nitrogen atom to which they are attached form a pyrrolidinyl, piperidino, morpholino, 4-N(R$^{11}$)-piperazinyl or imidazolyl group wherein said group is optionally substituted with methyl or OH:
R$^7$is H or C$_1$–C$_6$ alkyl;
R$^8$is C$_{1-C3}$ alkyl optionally substituted with NR$^5$R$^6$;
R$^9$ and R$^{10}$ together with the nitrogen atom to which they are attached form a pyrrolidinyl, piperidino, morpholino or 4-N(R$^{12}$)-piperazinyl group wherein said group is optionally substituted with C$_{1-C4}$ alkyl, C$_1$–C$_3$ alkoxy, NR$^{13}$R$^{14}$ or CONR$^{13}$R$^{14}$;
R$^{11}$ is H, C$_1$–C$_6$ alkyl optionally substituted with phenyl; (hydroxy)C$_2$–C$_3$ alkyl; or C$_1$–C$_4$ alkanoyl;
R$^{12}$ is H; C$_1$–C$_6$ alkyl; (C$_1$–C$_3$ alkoxy)C$_2$–C$_6$ alkyl; (hydroxy)C$_2$–C$_6$ alkyl; (R$^{13}$R$^{14}$ N)C$_2$–C$_6$ alkyl; CONR$^{13}$R$^{14}$; CSNR$^{13}$R$^{14}$; or C(NH)NR$^{13}$R$^{14}$; and
R$^{13}$ and R$^{14}$ are each independently H; C$_1$–C$_4$ alkyl, (C$_1$–C$_3$ alkoxy)C$_2$–C$_4$ alkyl; or (hydroxy)C$_2$–C$_4$ alkyl;
or a pharmaceutically acceptable salt thereof, or a pharmaceutical composition containing said compound, in a medicament for the curative or prophylactic treatment of erectile dysfunction in a male animal, including man.

In the above definition, unless otherwise indicated, alkyl groups having three or more carbon atoms, alkenyl and alkynyl groups having four or more carbon atoms, alkoxy groups having three carbon atoms and alkanoyl groups having four carbon atoms may be straight chain or branched chain. Halo means fluoro, chloro, bromo, or iodo.

The compounds of formula (I) may contain one or more asymmetric centers and thus they can exist as enantiomers or diasteriomers. Furthermore, certain compounds of formula (I) which contain alkenyl groups may exist as cis-isomers or trans-isomers. In each instance, the invention includes both mixtures and separate individual isomers.

The compounds of formula (I) may also exist in tautomeric forms and the invention includes both mixtures and separate individual tautomers.

A preferred group of compounds of formula (I) is that wherein $R^1$ is H, methyl, or ethyl; $R^2$ is $C_2$–$C_3$ alkyl; $R^3$ is $C_2$–$C_3$ alkyl or allyl; $R^4$ is $C_1$–$C_2$ alkyl optionally substituted with OH, $NR^5R^6$, CN, $CONR^5R^6$, or $CO_2R^7$; acetyl optionally substituted with $NR^5R^6$; hydroxyethyl optionally substituted with $NR^5R^6$; ethoxymethyl optionally substituted with OH or $NR^5R^6$; CH=CHCN; CH=CHCONR$^5$R$^6$; CH=CHCO$_2$R$^7$; CONR$^5$R$^6$; CO$_2$H; Br; NR$^5$R$^6$; NHSO$_2$NR$^5$R$^6$; NHSO$_2$R$^8$; SO$_2$NR$^9$R$^{10}$; or pyridyl or imidazolyl either of which is optionally substituted with methyl; $R^5$ and $R^6$ are each independently H, methyl, or ethyl, or together with the nitrogen atom to which they are attached form a piperidino, morpholino, 4-N($R^{11}$-piperazinyl or imidazolyl group wherein said group is optionally substituted with methyl or OH; $R^7$ is H or t-butyl; $R^8$ is methyl or $CH_2$ $CH_2$ $CH_2NR^5R^6$; $R^9$ and $R^{10}$ together with the nitrogen atom to which they are attached form a piperidino or 4-N($R^{12}$)-piperazinyl group wherein said group is optionally substituted with $NR^{13}R^{14}$ or $CONR^{13}R^{14}$; $R^{11}$ is H, methyl, benzyl, 2-hydroxyethyl or acetyl; $R^{12}$ is H, $C_1$–$C_3$ alkyl, (hydroxy)$C_2$–$C_3$ alkyl; $CSNR^{13}R^{14}$, or $C(NH)NR^{13}R^{14}$; and $R^{13}$ and $R^{14}$ are each independently H or methyl.

A more preferred group of compounds of formula (I) is that wherein $R^1$ is methyl, or ethyl; $R^2$ is $C_1$–$C_3$ alkyl; $R^3$ is ethyl, n-propyl, or allyl; $R^4$ is $CH_2NR^5R^6$, CH(OH) $CH_2NR^5R^6$, $CH_2OCH_2CH_3$, $CH_2OCH_2CH_2OH$, $CH_2OCH_2CH_2OHNR^5R^6$, CH=CHCON(CH$_3$)$_2$, CH=CHCO$_2$R$^7$; CONR$^5$R$^6$; CO$_2$H; Br; NHSO$_2$NR$^5$R$^6$; SO$_2$NR$^9$R$^{10}$; 2-pyridyl, 1-imidazolyl, or 1-methyl-2-imidazolyl; $R^5$ and $R^6$ together with the nitrogen atom to which they are attached form a piperidino, 4-hydroxypiperidino, morpholino, 4-N($R^{11}$)-piperazinyl or 2-methyl-1-imidazolyl group; $R^7$ is H or t-butyl; $R^9$ and $R^{10}$ together with the nitrogen atom to which they are attached form a 4-carbamoylpiperidino or 4-N($R^{12}$)-piperazinyl group; $R^{11}$ is H, methyl, benzyl, 2-hydroxyethyl or acetyl; and $R^{12}$ is H, $C_1$–$C_3$ alkyl, 2-hydroxyethyl, or $CSNH_2$.

A particularly preferred group of compounds of formula (I) is that wherein $R^1$ is methyl or ethyl; $R^2$ is n-propyl; $R^3$ is ethyl, n-propyl, or allyl; $R^4$ is $COCH_2NR^5R^6$, $CONR^5R^6$, $SO_2NR^9R^{10}$, or 1-methyl-2-imidazolyl; $R^5$ and $R^6$ together with the nitrogen atom to which they are attached form a morpholino or 4-N($R^{11}$)-piperazinyl group; $R^9$ and $R^{10}$ together with the nitrogen atom to which they are attached form a 4-N($R^{12}$)-piperazinyl group; $R^{11}$ is H, methyl or acetyl; and $R^{12}$ is H, methyl, 2-propyl, or 2-hydroxyethyl.

Especially preferred individual compounds for use in the present invention include:

5-[2-ethoxy-5-(4-methyl-1-piperazinylsulphonyl)-phenyl]-1-methyl-3-n-propyl-1,6-dihydro-7H-pyrazolo[4,3-d]pyrimidin-7-one (sildenafil);

5-(2-ethoxy-5-morpholinoacetylphenyl)-1-methyl-3-n-propyl-1,6-dihydro-7H-pyrazolo[4,3-d]pyrimidin-7-one;

5-(5-morpholinoacetyl-2-n-propoxyphenyl)-1-methyl-3-n-propyl-1,6-dihydro-7H-pyrazolo[4,3-d]pyrimidin-7-one;

5-[2-allyloxy-5-(4-methyl-1-piperazinylsulphonyl)-phenyl]-1-methyl-3-n-propyl-1,6-dihydro-7H-pyrazolo[4,3-d]pyrimidin-7-one;

5-{2-ethoxy-5-[4-(2-propyl)-1-piperazinylsulphonyl]-phenyl}-1-methyl-3-n-propyl-1,6-dihydro-7H-pyrazolo[4,3-d]pyrimidin-7-one;

5-{2-ethoxy-5-[4-(2-hydroxyethyl)-1-piperazinylsulphonyl]-phenyl}-1-methyl-3-n-propyl-1,6-dihydro-7H-pyrazolo[4,3-d]pyrimidin-7-one;

5-{5-[4-(2-hydroxyethyl)-1-piperazinylsulphonyl]-2-n-propoxyphenyl}-1-methyl-3-n-propyl-1,6-dihydro-7H-pyrazolo[4,3-d]pyrimidin-7-one;

5-[2-ethoxy-5-(4-methyl-1-piperazinylcarbonyl)-phenyl]-1-methyl-3-n-propyl-1,6-dihydro-7H-pyrazolo[4,3-d]pyrimidin-7-one; and 5-[2-ethoxy-5-(1-methyl-2-imidazolyl)-phenyl]-1-methyl-3-n-propyl-1,6-dihydro-7H-pyrazolo[4,3-d]pyrimidin-7-one.

The compounds of formula (I), and their pharmaceutically acceptable salts, processes for the preparation thereof, in vitro tests methods for determining cGMP PDE and cAMP PDE inhibitory activities thereof, are described in EP-A-0463756 and EP-A-0526004, the contents of which are hereby incorporated by reference.

The present inventors have found that intranasal administration of sildenafil, or derivatives thereof, effectively results in complete and very rapid absorption of these compounds into plasma. Intranasal administration of sildenafil, or derivatives thereof, is as effective as intravenous administration, but may be conveniently and painlessly self-administered by the patient. Intranasal administration can be employed at lower doses than oral administration, thereby allowing a decreased incidence of side effects.

According to the present invention, sildenafil, or derivatives thereof, may be administered either as a free base, or in the form of a pharmaceutically acceptable salt thereof. Pharmaceutically acceptable salts of the compounds of formula (I) which contain a basic center are, for example, non-toxic acid addition salts formed with inorganic acids such as hydrochloric, hydrobromic, sulphuric and phosphoric acid, with organo-carboxylic acids, or with organo-sulphonic acids. Compounds of the formula (I) can also provide pharmaceutically acceptable metal salts, in particular non-toxic alkali metal salts, with bases. Examples include sodium and potassium salts.

A still further aspect of this invention is a pharmaceutical composition of matter that comprises sildenafil, or derivatives thereof, as described above, and/or pharmaceutically acceptable salts thereof, and pharmaceutically acceptable carriers therefor.

For therapeutic use in the treatment of erectile impotence, sildenafil, or derivatives thereof, or its salt, can be conveniently administered in the form of a pharmaceutical composition containing sildenafil, or derivatives thereof, or its salt, and a pharmaceutically acceptable carrier therefor. Typically, the carrier may be a liquid, solution, suspension, gel, or combinations thereof. In a preferred embodiment, the carrier is a pharmaceutically acceptable aqueous solution. Such compositions may require the use of one or more solubilizing agents to both effect dissolution of the drug(s) and/or keep them in aqueous solution. Such solubilizing agents include, but are not limited to nicotinamide, sodium saccharin, propylene glycol, glycerin, ethyl alcohol, etc. Suitable applications of solubilizing agents are exemplified below. Compositions according to the present invention may be prepared in accordance with accepted pharmaceutical procedures, for example, as described in *Remington's Pharmaceutical Sciences*, seventeenth edition, ed. Alfonso R. Gennaro, Mack Publishing Company, Easton, Pa., Eighteenth edition (1990), which is hereby incorporated by reference.

The compound of the invention or its salt may be formulated together with the carrier into any desired unit dosage form. Unit dosage forms such as solutions, suspensions, and water-miscible semisolids are particularly preferred.

Each carrier must be "acceptable" in the sense of being compatible with the other ingredients in the formulation and not injurious to the patient. The carrier must be biologically acceptable and inert. In most cases, suitable buffers are included in the carriers to maintain the pH within the limits required to keep the drugs in solution. For example, for drugs containing a basic center, the solutions are buffered in the acidic pH range (approximately 2 to 6), and for drugs containing an acidic center, the solutions are buffered in the alkaline pH range (approximately 8 to 12). To prepare formulations suitable for intranasal administration, solutions and suspensions are sterilized and are preferably isotonic to blood.

In addition to sildenafil and the ingredients particularly mentioned above, the formulations of this invention may also include other drugs used in the treatment of erectile dysfunction. Such additional drugs include, but are not limited to, apomorphine, papaverine, phentolamine, and phenoxybenzamine.

According to the present invention, the term "patient" will encompass any mammal requiring treatment with sildenafil, or derivatives thereof, particularly a male human patient suffering from erectile impotence. In addition to the medical treatment of humans, this invention will also be applicable to the breeding of animals, such as horses and dogs, where artificial insemination may be prohibited.

The dosage of sildenafil, or derivatives thereof, or pharmaceutically acceptable salts thereof in the compositions of the invention will vary depending on several factors, including, but not limited to, the age, weight, and species of the patient, the general health of the patient, the severity of the symptoms, whether the composition is being administered alone or in combination with other agents, the incidence of side effects and the like. The desired dose may be administered as needed, and may be administered repeatedly over a period of months or years. Higher and lower doses may also be administered. A major advantage of the present invention is the extremely rapid onset of response, which enables the patient to adjust the dose to produce only the desired effects and nothing more, thereby optimizing drug use and minimizing side-effects.

The daily dose may be adjusted taking into account, for example, the above-identified variety of parameters. Typically, sildenafil, or derivatives thereof, may be administered in an amount of up to about 400 mg/day. Preferably, the amount of sildenafil, or derivatives thereof, administered will not exceed 300 mg/day. However, other amounts may also be administered, in particular, much smaller amounts of sildenafil, or derivatives thereof, will be required when administered intranasally, in accordance with the present invention.

To achieve good plasma concentrations, the sildenafil, or derivatives thereof, may be administered, for instance, by intranasal administration of an approximate 0.1 to 1M solution of the active ingredient, optionally in saline.

While it is possible for the active ingredient to be administered alone, it is preferably present as a pharmaceutical formulation. The formulations of the present invention comprise at least one active ingredient, as defined above, together with one or more acceptable carriers thereof and optionally other therapeutic agents.

The above method may be practiced by administration of the compounds by themselves or in a combination with other active ingredients in a pharmaceutical composition. Other therapeutic agents suitable for use herein are any compatible drugs that are effective by the same or other mechanisms for the intended purpose, or drugs that are complementary to those of the present agents. Such additional drugs include, but are not limited to, apomorphine, papaverine, phentolamine, and phenoxybenzamine. The compounds utilized in combination therapy may be administered simultaneously, in either separate or combined formulations, or at different times than the present compounds, e.g., sequentially, such that a combined effect is achieved. The amounts and regime of administration will be adjusted by the practitioner, by preferably initially lowering their standard doses and then titrating the results obtained. The therapeutic method of the invention may be used in conjunction with other therapies as determined by the practitioner.

Having now generally described this invention, the same will be better understood by reference to certain specific examples, which are included herein for purposes of illustration only and are not intended to be limiting of the invention or any embodiment thereof, unless so specified. Set forth below are examples of experimental procedures designed to demonstrate the features of this invention in animal models, and examples of pharmaceutical dosage forms that embody and illustrate its reduction to practice.

EXAMPLE 1

ABSORPTION OF SOLUBILIZED SILDENAFIL FROM THE NASAL CAVITY OF RATS

Experimental Technique

These experiments determine the bioavailability of sildenafil, or derivatives thereof, after nasal administration and compare it to that after intravenous administration. In particular, the present experiment determined the absorption of sildenafil into the blood of rats following intranasal administration of a formulation in which the sildenafil was solubilized by the addition of mesylic acid (see below).

The nasal absorption of sildenafil, or derivatives thereof, were measured using an in vivo technique in rats. Rats were fasted overnight prior to experimentation. Surgical procedures were performed under equithesin anesthesia (3 ml/kg, i.p.). An incision was made in the neck of each rat, and the trachea cannulated with polyethylene tubing (PF-260). A closed end tube was inserted through the esophagus to the posterior part of the nasal cavity to prevent drug from entering the esophagus. The nasopalatine passage was closed with an adhesive agent to prevent drainage of the drug from the nasal cavity to the mouth.

The jugular vein and femoral artery were cannulated with polyethylene tubing for intravenous drug administration and intra-arterial blood sampling.

Solutions of sildenafil hydrochloride (2 and 4 mg/rat/50 $\mu$l) were prepared in water and administered through the right nostril using a microsyringe. For intravenous administration, the same dose of the drug was injected into the jugular vein (1 ml/kg body weight). Blood samples after nasal or intravenous drug administration were collected before and at 2, 15, 30, 60 and 120 min after drug administration, centrifuged, and serum removed and stored (−80° C.) until analysis.

Bioavailability of nasally administered drug was calculated by comparing the plasma drug concentrations between nasal and intravenous delivery routes and expressed as a percentage of the intravenous bioavailability.

Formulation of the Intranasal Dosage Form

The main problem with preparing an intranasal dosage form of sildenafil is the limited solubility (3.5 mg/ml) of the citrate salt in water. This was overcome by solubilizing the sildenafil citrate with mesylic acid.

The solution instilled into the nasal cavities of the rats in this experiment had the following composition:

Sildenafil Citrate 10 mg

Mesylic Acid Solution (0.15 Nl) 200 microliters

Adjust the pH to 2.8 to 3.0 with 0.05M NaOH

The resulting solution was clear with no precipitation for over one month at room temperature.

Assay Method for Sildenafil in Rat Blood

At various times following the intranasal and intravenous administration of sildenafil to rats, the concentrations of sildenafil in blood were determined using the following analytical method:

One hundred microliters of rat plasma was treated with 25 microliters of 1M monochloroacetic acid to denature the plasma proteins and release free sildenafil. Seventy-five microliters of acetonitrile was then added to precipitate the proteins. This solution was centifuged for 5 minutes at 5,000 g. The clear supernatant was injected onto the HPLC column.

The HPLC system consisted of the following:

| | |
|---|---|
| Column: | Supelco Kromasil $C_4$ 4.6 mm × 150 mm |
| Mobile Phase: | Water, acetonitrile, 0.5M potassium phosphate buffer (pH 4.5) - 68, 28, 4. (The aqueous phase contained 10 mM diethylamine hydrochloride.) |
| Flow Rate: | 2 ml/min |
| Detection: | UV @230 nm |

Results

The mean concentrations (+/− standard deviations) of sildenafil found in the blood of rats at various times following the intranasal (n=5) and intravenous administrations (n=3) of the sildenafil solution described above are shown in Table 1. The concentrations are expressed as areas under the HPLC curves×$10^{-4}$.

Comparing the areas under the blood concentration versus time curves (see FIG. 1) shows that sildenafil is rapidly and complete absorbed following intranasal administration, and the peak blood concentration occurs at approximately 10 to 15 minutes following intranasal administration. These results indicate that the intranasal route produces much more rapid response in humans than does the current oral tablet formulation for which peak plasma concentrations are not achieved until 60 to 120 minutes following administration.

TABLE 1

Concentration* of Sildenafil In the Blood of Rats

| | Intravenous Administration | | Intranasal Administration | |
|---|---|---|---|---|
| Time (min) | Mean (n = 3) | Standard Deviation | Mean (n = 5) | Standard Deviation |
| 0 | 188.8 | 21.0 | 11.7 | 1.3 |
| 2 | 84.7 | 11.3 | 12.1 | 1.0 |
| 5 | 47.7 | 2.9 | 25.5 | 13.7 |
| 10 | 32.0 | 2.7 | 38.2 | 7.9 |
| 15 | 19.5 | 4.9 | 43.5 | 19.8 |
| 20 | 17.9 | 7.4 | 32.6 | 20.2 |
| 30 | 16.0 | 4.1 | 31.0 | 7.9 |
| 40 | 14.6 | 1.3 | 22.7 | 9.5 |
| 50 | 7.6 | 1.4 | 19.6 | 1.0 |

*Concentrations are expressed as area under the HPLC curve × 10

EXAMPLE 2

NASAL SPRAY SOLUTION

| | |
|---|---|
| Sildenafil hydrochloride | 15 g |
| 0.05M Phosphate Buffer, pH 4.4 | 100 ml |
| Sodium chloride | q.s. ad isotonicity |

The sildenafil is dissolved in the buffer and sufficient sodium chloride is added to the solution to make it isotonic. The solution is placed in a nasal administrator designed to deliver 100 μl of spray for each application. One spray in each nostril will deliver a total of 30 mg of sildenafil hydrochloride.

EXAMPLE 3

NASAL GEL (AQUEOUS)

| | |
|---|---|
| Sildenafil hydrochloride | 15 g |
| Methocel | 3 g |
| 0.05M Acetate buffer, pH 4.4 | 100 g |

Approximately 70 g of buffer is heated to 80° C., and the methocel is dispersed in it with stirring. The sildenafil hydrochloride is dissolved in 30 g of buffer at 80° C., and the solution is mixed with the methocel dispersion. The resultant mixture is allowed to stand at room temperature for 3 hours. The gel is placed in an ointment tube equipped with a fine orifice and is applied in the nasal nares with a finger or cotton tipped applicator.

EXAMPLE 4

COMBINATION NASAL SPRAY SOLUTION

| | |
|---|---|
| Sildenafil hydrochloride | 15 g |
| Apomorphine hydrochloride | 500 mg |
| 0.05M Phosphate Buffer, pH 4.4 | 100 ml |
| Sodium chloride | q.s. ad isotonicity |

The sildenafil hydrochloride and apomorphine hydrochloride are dissolved in the buffer and sufficient sodium chloride is added to the solution to make it isotonic. The solution is placed in a nasal administrator designed to deliver 100 μl of spray for each application. One spray in each nostril will deliver a total of 30 mg of sildenafil hydrochloride and 1 mg of apomorphine hydrochloride.

EXAMPLE 5

COMBINATION NASAL GEL (AQUEOUS)

| | |
|---|---|
| Sildenafil hydrochloride | 15 g |
| Apomorphine hydrochloride | 500 mg |
| Methocel | 3 g |
| 0.05M Acetate buffer, pH 4.4 | 100 g |

Approximately 70 g of buffer is heated to 80° C., and the methocel is dispersed in it with stirring. The sildenafil hydrochloride and apomorphine hydrochloride are dissolved in 30 g of buffer at 80° C., and the solution is mixed with the methocel dispersion. The resultant mixture is allowed to stand at room temperature for 3 hours. The gel is placed in an ointment tube equipped with a fine orifice and is applied in the nasal nares with a finger or cotton tipped applicator.

While the invention has been described and illustrated herein by references to various specific material, procedures and examples, it is understood that the invention is not restricted to the particular material, combinations of material, and procedures selected for that purpose. Numerous variations of such details can be implied and will be appreciated by those skilled in the art.

What is claimed is:

1. A method for rapidly and reliably delivering sildenafil to the systemic circulation of a patient for the treatment of erectile dysfunction comprising intranasally administering an effective amount of a pharmaceutical composition comprising sildenafil, or a pharmaceutically acceptable salt thereof, and a pharmaceutically acceptable carrier therefor.

2. A method according to claim 1, wherein the pharmaceutically acceptable salt of sildenafil is sildenafil HCl.

3. A method according to claim 1, wherein the carrier is aqueous.

4. A method according to claim 1, wherein sildenafil is combined with apomorphine or a pharmaceutically acceptable salt thereof.

5. A method according to claim 1, wherein sildenafil is combined with one or more vasoactive drugs selected from the group consisting of phenoxybenzamine, phentolamine, papaverine, and pharmaceutically acceptable salts thereof.

6. A method for treating erectile impotence comprising intranasally administering to a patient in need of such treatment an effective amount of sildenafil, or a pharmaceutically acceptable salt thereof.

7. A method according to claim 6, wherein sildenafil is combined with one or more vasoactive drugs selected from the group consisting of phenoxybenzamine, phentolamine, papaverine, and pharmaceutically acceptable salts thereof.

8. A method according to claim 6, wherein the wherein the pharmaceutically acceptable salt of sildenafil is sildenafil HCl.

9. A method according to claim 7, wherein the sildenafil, or a pharmaceutically acceptable salt thereof is carrier is aqueous.

10. A pharmaceutical composition suitable for intranasal administration comprising sildenafil, or a pharmaceutically acceptable salt thereof, and a pharmaceutically and intranasally acceptable carrier therefor.

11. A pharmaceutical composition according to claim 10, further comprising one or more vasoactive drugs selected from the group consisting of phenoxybenzamine, phentolamine, papaverine, and pharmaceutically acceptable salts thereof.

12. A composition according to claim 7, wherein the pharmaceutically acceptable salt of sildenafil is sildenafil HCl.

* * * * *